US007217490B2

(12) United States Patent
Barclay et al.

(10) Patent No.: US 7,217,490 B2
(45) Date of Patent: May 15, 2007

(54) PROCESSES FOR PRODUCING SILANE MONOMERS AND POLYMERS AND PHOTORESIST COMPOSITIONS COMPRISING SAME

(75) Inventors: George G. Barclay, Jefferson, MA (US); Subbareddy Kanagasabapathy, Worcester, MA (US); Matthew A. King, Boston, MA (US)

(73) Assignee: Shipley Company, L.L.C., Marlborough, MA (US)

( * ) Notice: Subject to any disclaimer, the term of this patent is extended or adjusted under 35 U.S.C. 154(b) by 0 days.

(21) Appl. No.: 10/378,553

(22) Filed: Mar. 3, 2003

(65) Prior Publication Data

US 2003/0219676 A1 Nov. 27, 2003

(51) Int. Cl.
*G03C 1/73* (2006.01)
*G03F 7/039* (2006.01)
*C07F 7/12* (2006.01)

(52) U.S. Cl. .................. 430/270.1; 430/326; 430/905; 430/914; 556/437; 556/440

(58) Field of Classification Search ............ 430/270.1, 430/325, 326, 914, 311, 271.1, 272.1; 556/440
See application file for complete search history.

(56) References Cited

U.S. PATENT DOCUMENTS 3,969,543 A 7/1976 Roberts et al. ............... 427/54
4,745,169 A 5/1988 Sugiyama et al. ............ 528/43
5,100,503 A 3/1992 Allman et al. .............. 156/643
5,240,813 A 8/1993 Watanabe et al. ........... 430/280
5,547,808 A 8/1996 Watanabe ................... 430/176
5,612,170 A 3/1997 Takemura et al. ....... 430/270.1
5,691,396 A 11/1997 Takemura et al. ............ 522/62
5,731,126 A 3/1998 Takemura et al. ....... 430/270.1
5,733,978 A * 3/1998 Kobayashi .................. 525/100
5,882,844 A 3/1999 Tsuchiya et al. ......... 430/288.1
5,972,560 A 10/1999 Kaneko et al. .......... 430/270.1
6,087,064 A 7/2000 Lin et al. ................. 430/270.1
6,210,856 B1 4/2001 Lin et al. ................. 430/270.1
6,309,796 B1 10/2001 Nakashima et al. ..... 430/287.1
6,342,562 B1 1/2002 Kozawa et al. ............. 524/588
6,420,084 B1 7/2002 Angelopoulos et al. .. 430/270.1
6,420,088 B1 7/2002 Angelopoulos et al. .. 430/272.1

FOREIGN PATENT DOCUMENTS

WO WO 02/091083 A1 11/2002

* cited by examiner

*Primary Examiner*—Sin Lee
(74) *Attorney, Agent, or Firm*—Peter F. Corless; Darryl P. Frickey; Edwards Angell Palmer & Dodge LLP

(57) ABSTRACT

The invention includes new Si-containing monomers, polymers containing such monomers and photoresists that contain the polymers. Synthetic methods of the invention include reacting a vinyl carbocyclic aryl ester compound with a reactive silane compound to provide the monomer.

18 Claims, No Drawings

PROCESSES FOR PRODUCING SILANE MONOMERS AND POLYMERS AND PHOTORESIST COMPOSITIONS COMPRISING SAME

BACKGROUND OF THE INVENTION

1. Field of the Invention

The present invention relates to new Si-containing monomers and methods of synthesis of such monomers; polymers produced from such monomers; and photoresists that contain such polymers as a resin components. Photoresists of the invention are particularly useful for multilayer lithographic processing.

2. Background

Photoresists are photosensitive films used for transfer of images to a substrate. A coating layer of a photoresist is formed on a substrate and the photoresist layer is then exposed through a photomask to a source of activating radiation. The photomask has areas that are opaque to activating radiation and other areas that are transparent to activating radiation. Exposure to activating radiation provides a photoinduced chemical transformation of the photoresist coating to thereby transfer the pattern of the photomask to the photoresist-coated substrate. Following exposure, the photoresist is developed to provide a relief image that permits selective processing of a substrate.

A photoresist can be either positive-acting or negative-acting. For most negative-acting photoresists, those coating layer portions that are exposed to activating radiation polymerize or crosslink in a reaction between a photoactive compound and polymerizable reagents of the photoresist composition. Consequently, the exposed coating portions are rendered less soluble in a developer solution than unexposed portions. For a positive-acting photoresist, exposed portions are rendered more soluble in a developer solution while areas not exposed remain comparatively less developer soluble.

The increasing density of integrated circuits has created a need for higher resolution patterning capabilities. One method of improving resolution involves using a shorter wavelength light during pattern formation. Shorter wavelengths of approximately 200 to 280 nm may be obtained by using a deep UV ("DUV") source such as a mercury/xenon ("Hg/Xe") lamp with appropriate filters. Additionally, KrF (248 nm) or ArF (193 nm) excimer lasers may be used as exposure sources.

In addition to using shorter wavelengths during exposure, it is also desirable to use a thinner layer of resist. However, the major drawback of using a thin layer of resist is that the variation of resist thickness over a diffusion step on a substrate and into an etched pattern increases as the pattern size becomes smaller. This variation means that the dimensions of any pattern being imaged in the resist will vary as the step geometry is traversed. Therefore, in a single layer resist system, the lack of dimensional control on the wafer can create different line widths throughout the resist which reduces the quality of the electronic package.

To improve dimensional control, bilayer (or bilevel or multilevel) resist systems have been utilized. In a typical bilevel system, a bottom resist is first applied to a substrate to planarize wafer topography. The bottom resist is cured and a second thinner imaging top resist is then applied over the bottom resist. The top resist is then soft baked, and patterned (or imaged) using conventional resist exposure and development, followed by etch transfer of the top pattern through the bottom resist using the top resist pattern as an etch mask. See, generally, Sugiyama et al., *Positive Excimer Laser Resists Prepared with Aliphatic Diazoketones, Soc. Plastics Eng., Conference Proceedings,* pages 51–60 (November 1988); and U.S. Pat. Nos. 4,745,169; 5,338,818; 5,691,396; 5,731,126; 6,296,985; and 6,340,734.

SUMMARY OF THE INVENTION

We have now found novel Si-containing monomer and siloxane polymers produced therefrom and methods for synthesis of these monomer and polymers. Polymers produced through methods of the invention are particularly useful as a photoresist resin component.

Preferred monomer syntheses of the invention include reacting a vinyl carbocyclic aryl ester compound with a reactive silane compound.

Preferably, the carbocyclic aryl compound is a substituted phenyl compound, e.g. a compound of the formula $CH_2{=}CH{-}C_6H_4$-ester. That ester group is preferably of the formula $-OC({=}O)R$ wherein R is optionally substituted $C_{1-6}$alkyl, preferably an acetyl group i.e. $-OC({=}O)CH_3$. The phenyl group can be substituted in any number of positions e.g. 1,4-substituted or 1,3-substituted. The carbocyclic group also may be suitably substituted at ring positions by groups other than an alkene and ester, e.g. by halo, $C_{1-8}$alkoxy, $C_{1-8}$alkyl, nitro, cyano, etc.

A variety of reactive silane reagents may be employed, with trihalosilanes, trihydroxysilanes, and trialkoxysilanes being preferred. Particularly preferred are trihalosilanes, especially trichlorosilane.

Preferably, the silane compound and the substituted carbocyclic aryl compound are reacted in the presence of a phosphine reagent such as a triphenylphosphine or other suitable phosphine reagent. Even more preferred is to conduct the reaction in the presence of a metal catalyst, such as a palladium reagent, particularly a Pd(II) compound.

The reaction preferably adds the silane reagent across the vinyl group, particularly forming a carbon-Si bond to the more substituted alkene carbon. In the case of a vinyl phenyl compound, the reaction preferably provides a benzylic silane group. More particularly, by reacting the carbocyclic aryl compound of $CH_2{=}CH{-}C_6H_4$-ester with a trihalosilane, a preferred reaction product is $CH_3CH(Si(halo)_3){-}C_6H_4$-ester. That monomer then can be polymerized to provide a siloxane polymer. As discussed below, preferred methods of polymerization include polymerizing the Si-monomer in the presence of compound having multiple reactive nitrogen moieties to provide the siloxane polymer Polymers of the invention are particularly useful as a resin component of a photoresist composition Typical photoresist compositions of the invention will contain a photoactive component, e.g. one or more photoacid generator compounds. Chemically-amplified positive-acting photoresists will contain a component that has one or more photoacid-labile deblocking groups, e.g. a photoacid-labile acetal or ester group such as t-butylester or adamantylester. Such photoacid-labile group(s) suitably will be substituents of silicon-containing resin, e.g. the photoacid-labile moiety may be grafted onto a phenolic group of a formed polymer, but the resist also may contain a separate component such as a separate oligomer or polymer that contains such photoacid-labile group(s). Negative-acting resists of the invention typically will contain an agent for crosslinking of one or more components of the resist, typically a separate crosslinker component such as an amine-based reagent, e.g. a melamine or benzoguanamine resin.

Photoresists of the invention are particular useful for imaging at deep UV wavelengths, particularly sub-300 nm wavelengths such as about 248 nm. Photoresists of the invention also can be imaged at shorter wavelengths, e.g. sub-200 nm such as 193 nm and 157 nm.

Photoresists of the invention are preferably employed in multilayer lithography systems. More particularly, preferred uses of resists of the invention include application of a first organic polymer coating on a substrate, e.g. a microelectronic wafer, and applying thereover a photoresist of the invention. The organic bottom layer suitably may be non-photoimageable (e.g. not contain a photoacid generator compound) but thermally crosslinked prior to application of the top resist layer. The bottom layer may comprise a phenolic polymer such as a novolac admixed with a thermal acid generator compound and a crosslinker. Use of such a bottom layer can enable application of very thin top resist layer.

The invention also provides methods for forming relief images, including methods for forming a highly resolved relief image such as a pattern of lines where each line has essentially vertical sidewalls and a line width of about 0.40 microns or less, and even a width of about 0.25, 0.20 or 0.16 microns or less. The invention further provides articles of manufacture comprising substrates such as a microelectronic wafer substrate, optoelectronic substrate or liquid crystal display or other flat panel display substrate having coated thereon a polymer, photoresist or resist relief image of the invention. The invention also includes methods to produce such articles of manufacture, which comprises use of a photoresist of the invention.

The invention also includes monomers and polymers obtainable or obtained by a method of the invention. Other aspects of the invention are disclosed infra.

DETAILED DESCRIPTION OF THE INVENTION

As discussed above, preferred monomer syntheses of the invention include reacting a vinyl carbocyclic aryl ester compound with a reactive silane compound.

The following exemplary Scheme I depicts a preferred synthesis of the invention with preferred reagents and conditions. It will be understood however that a variety of other compounds and conditions can be employed in a similar manner as described below with respect to the exemplified compounds and conditions.

SCHEME I

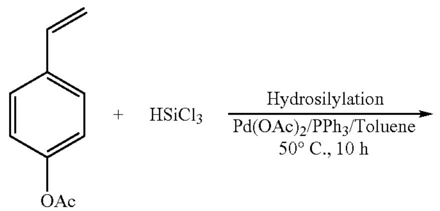

1 2

-continued

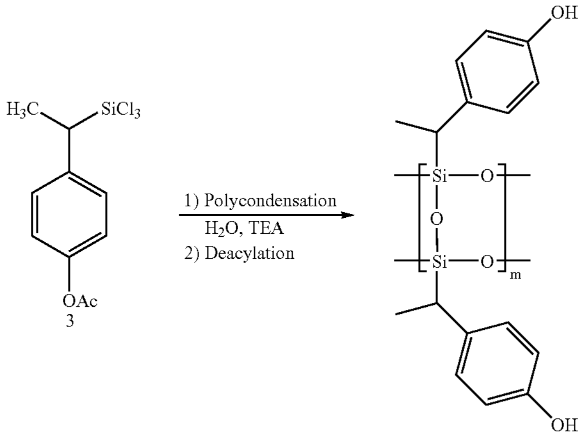

3

4

As shown in Scheme I, vinyl, ester carbocyclic aryl compound 1 is reacted with reactive silane reagent 2, which is shown as a preferred trihalosilane reagent. As discussed above, the reaction is preferably conducted in the presence of a phosphine reagent such as a triphenylphoshine and even more preferably in the presence of a metal catalyst, such as a platinum, nickel, palladium or other suitable catalyst, preferably a palladium catalyst such as a Pd(II) reagent.

The reaction can be conducted under a variety of conditions. Optimal reaction conditions can be readily determined empirically for any particular system. One particular protocol provide charging a reaction vessel with the substituted carbocyclic aryl reagent and phosphine and metal catalyst if employed in a suitable solvent such as tetrahydrofuran or an aromatic solvent such as toluene or xylenes. To that mixture, the reactive silane reagent can be added over time, and the complete reaction mixture stirred until reaction completion, typically at an elevated temperature such as at least about 40° C., 50° C., 60° C. or 70° C. to provide monomer 3. See Example 1 which follows for exemplary preferred reaction conditions.

Monomer 3 then can be polymerized with itself or with other monomers to form higher order polymers. After formation of polymer 4, the ester of the carbocyclic aryl group can be cleaved (e.g. hydrolyzed) to provide the corresponding carbocyclic aryl with alcohol substitution, e.g. a phenolic group as generally exemplified by polymer 4 in Scheme I above. The ester can suitably be deprotected by treatment with strong base or other appropriate procedure. The thus produced carbocyclic aryl alcohol (e.g. phenol) also then can be further functionalized, e.g. by reaction with a vinyl ether to provide a photoacid-labile acetal group, or with acid chloride to provide a photoacid-labile ester. The value m of polymer 4 suitably can vary widely for any particular polymer, e.g. from 5 to 10,000, more typically 10, 20, 30, 40, 50, 80 or 100 to about 1,000, 2,000, 3,000, 4,000 or 5,000, at least for many photoresist applications.

As mentioned above, preferred methods for polymerizing a monomer produced in accordance with the invention include reacting the monomer in the presence of compound having multiple reactive nitrogen moieties to provide a siloxane polymer.

Without being bound by any theory, it is believed the poly-nitrogen compound can serve as an effective "template" onto which the reactive silane compounds reagents can link during the course of the polymerization. The nitrogen compound then substantially withdraws from the polymer matrix and is not substantially incorporated into the final polymer. Such withdrawal of the nitrogen compound is facilitated by the relatively weak Si—N bond that is believed to exist during the "templating" process. Some amounts of the nitrogen-containing compound may be incorporated into the polymer, but typically at least about 60, 70, 80 or 90 mole percent of the nitrogen-containing compound utilized in a reaction is not incorporated into the final polymer.

In a preferred aspect, a plurality of distinct silane reagents may be employed in the polymerization reaction, e.g. at least two, three or four distinct silane reagents are polymerized to provide the corresponding copolymer, terpolymer, tetrapolymer or pentapolymer. For example, one silane reagent may have a photoacid-labile substituent such as a photoacid-labile ester or acetal, and another distinct silane reagent may have a dissolution control group such as a hexafluoropropanol group. Suitably, such groups may be substituents of a carbon alicyclic or heteroalicyclic moiety of a silane reagent.

The nitrogen-containing "templating" reagent preferably comprises one or more amine groups. Primary amines are generally preferred, but secondary and even tertiary amines also will be useful.

Particularly preferred nitrogen-containing "templating" reagents are small molecules, e.g. having a molecular weight of less than about 500, more preferably a molecular weight of less than about 400, 300, 200 or even 100. Such small molecules facilitate optimal positioning of the silane reagents during the polymerization.

Particularly preferred nitrogen-containing "templating" reagents also have a relatively rigid structure to further optimize positioning of silane reagents during the polymerization reaction. Thus, cyclic compounds having nitrogen substitution are preferred templating reagents, such as carbon alicyclic, heteroalicyclic, carbocyclic aryl or heteroaromatic compounds having one or preferably two or more nitrogen groups either as ring members or as substituents to the cyclic compound. Carbon alicyclic, heteroalicyclic, carbocyclic aryl or heteroaromatic compounds having multiple amine substituents are particularly preferred. An especially preferred templating reagent is a diamine phenyl compound.

While such more rigid templating reagents may be particularly preferred for at least some applications, non-cyclic templating reagents also will be effective such as a noncyclic $C_{1-12}$ alkyl or $C_{1-12}$ alkoxy having one or more nitrogen moieties, particularly amine moieties.

The following Scheme II depicts a preferred polymerization method as discussed above. For the purposes of exemplification only, particularly preferred compounds, reagents and conditions are depicted in the following Scheme II, and as with Scheme I, it will be understood that a variety of other compounds and conditions can be employed in a similar manner as described below with respect to the exemplified compounds and conditions. For instance, in Scheme II below, a number of preferred silane reagent substituents ($R_1$) that are not displaced during the reaction are depicted; a wide variety of other non-displaced substituents also may be employed. Scheme II also depicts the particularly preferred nitrogen-containing templating reagent of 1,4-diamine phenyl, but a variety of other templating reagents also may be employed.

SCHEME II

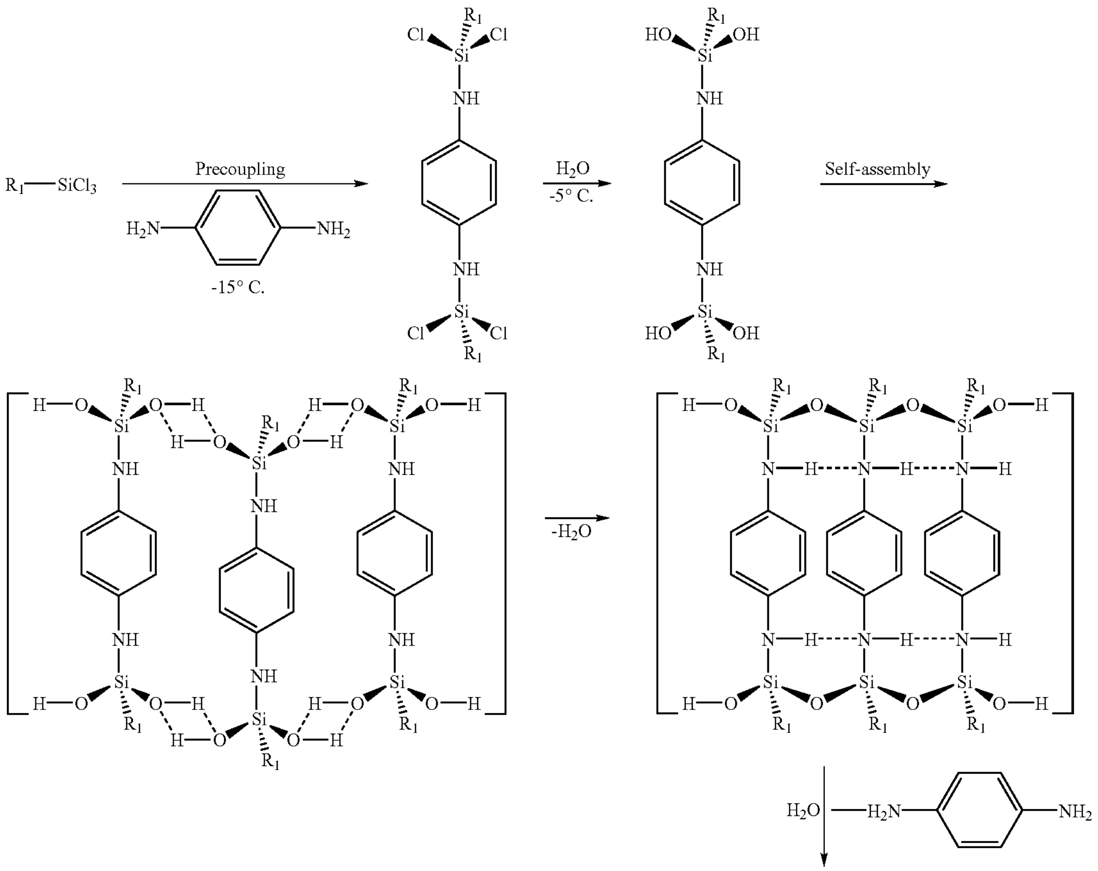

-continued

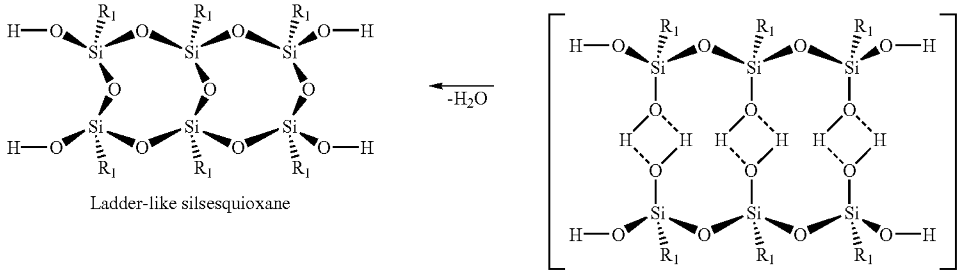

Ladder-like silsesquioxane

Thus, as shown in the above Scheme II, reactive silane compound $R_1$—$SiCl_3$ wherein R1 is preferably the protected carbocyclic aryl group shown in Scheme I above, is admixed with the compound having multiple nitrogen groups (1,4-diaminophenyl). Suitably, the silane and templating compounds are admixed at reduced temperatures e.g. 0° C. or less and in a suitable solvent such as tetrahydrofuran or other ether, or an aromatic solvent such as toluene, xylenes, and the like.

Preferably the reaction is conducted in the presence of base, e.g. an organic base such as triethylamine. Suitably, the nitrogen-containing compound can be added over time to a reaction vessel charged with one or more silane reagents.

After the reaction addition is complete, a slight molar excess (relative to silane reagent(s)) of water can be added to the reaction mixture to promote the self-assembly reaction. The reaction mixture then may be stirred and significantly neutralized by addition of water and dried, e.g. by addition of anhydrous sodium sulfate with overnight stirring.

Removal of the complexed nitrogen-containing templating reagent can be accomplished by the further addition of water and base (e.g. an organic base such as triethylamine) and increased reaction temperature, e.g. to above room temperature such as to about 40° C., 50° C., 60° C., 70° C. or greater. The reaction mixture can be agitated at such elevated temperature until reaction completion, e.g. 12, 24, 26, 48, 74 or more hours. At that point, the reaction mixture can be neutralized and the polymer isolated, washed and dried. See Example 2 which follows for exemplary preferred reaction conditions, As discussed above, the protected ester (e.g. acetoxy) of the silyl compound can be deprotected such as by basic hydrolysis after formation of the polymer to provided the carbocyclic aryl alcohol, particularly the phenol as depicted in Scheme I above.

As referred to herein, alkyl groups typically have from 1 to about 16 carbon atoms, more preferably 1 to about 8 carbon atoms, still more preferably 1, 2, 3, 4, 5, or 6 carbon atoms. As used herein, the term alkyl unless otherwise modified refers to both cyclic and noncyclic groups, although of course cyclic groups will comprise at least three carbon ring members.

Preferred alkoxy groups as referred to herein include those groups having one or more oxygen linkages and from 1 to about 16 carbon atoms, more preferably from 1 to about 8 carbon atoms, and still more preferably 1, 2, 3, 4, 5 or 6 carbon atoms.

Preferred amine groups include aminoalkyl groups include those groups having one or more primary, secondary and/or tertiary amine groups, and from 1 to about 12 carbon atoms, more preferably 1 to about 8 carbon atoms, still more preferably 1, 2, 3, 4, 5, or 6 carbon atoms.

Suitable heteroaromatic groups as referred to herein may have one or more fused or linked rings typically 1, 2 or 3 rings and at least one ring containing 1, 2 or 3 N, O or S atoms such as coumarinyl including 8-coumarinyl, quinolinyl including 8-quinolinyl, pyridyl, pyrazinyl, pyrimidyl, furyl, pyrrolyl, thienyl, thiazolyl, oxazolyl, oxidizolyl, triazole, imidazolyl, indolyl, benzofuranyl and benzothiazole.

Suitable carbocyclic aryl groups as referred to herein include multiple ring compounds that contain separate and/or fused aryl groups. Typical carbocyclic aryl groups contain 1 to 3 separate or fused rings and from 6 to about 18 carbon ring atoms. Specifically preferred carbocyclic aryl groups include phenyl; naphthyl including 1-naphthyl and 2-naphthyl; biphenyl; phenanthryl; anthracyl; and acenaphthyl.

As discussed above, polymers of the invention preferably comprise one or more repeat units that comprise a photoacid-labile group. The photoacid-labile group may be e.g. linked to the deprotected hydroxy substitutent of the carbocyclic aryl group incorporated into the polymer, e.g. the photoacid-labile group may be grafted onto the phenolic group of the polymer depicted in Scheme I. As discussed above, the photoacid-labile group may be e.g. an acid-labile ester The photoacid-labile group also may be e.g. an acetal group such as many be provided by reaction of a vinyl ether with a hydroxy substituent of a polymer repeat unit.

As discussed, various polymer moieties may be optionally substituted. A "substituted" substituent may be substituted at one or more available positions, typically 1, 2, or 3 positions by one or more suitable groups such as e.g. halogen (particularly F, Cl or Br); cyano; $C_{1-8}$ alkyl; $C_{1-8}$ alkoxy; $C_{1-8}$ alkylthio; $C_{1-8}$ alkylsulfonyl; $C_{2-8}$ alkenyl; $C_{2-8}$ alkynyl; hydroxyl; nitro; alkanoyl such as a $C_{1-6}$ alkanoyl e.g. acyl and the like; etc.

Particularly preferred polymer produced by methods of the invention include those that contain one or more repeat units provided by monomers of the following formulae I and/or II:

$(R^1SiO_{3/2})$ (I)

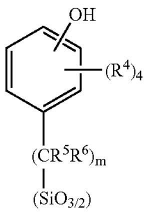

(II)

wherein $R^1$ is selected from $(C_1$–$C_{12})$alkyl, substituted $(C_1$–$C_{12})$alkyl, $(C_2$–$C_6)$alkenyl, substituted $(C_2$–$C_6)$alkenyl, phenyl, $C_6(R^7)_5$, $(C_1–C_5)$alkyl$(C_6(R^7)_4)$, $(C_1–C_5)$alkyl $(C_6H_4OZ)$, vinyl and substituted vinyl; Z is selected from $(C_1–C_6)$alkylsulfonate ester or arylsulfonate ester; each $R^7$ is independently selected from H, F, $(C_1–C_6)$alkyl, $(C_1–C_6)$alkoxy, halo$(C_1–C_6)$alkyl, hydroxy-halo$(C_1–C_6)$alkyl or halo$(C_1–C_6)$alkoxy;

each $R^4$ is independently selected from $R^7$ and OH; each $R^5$ is independently selected from H or F; each $R^6$ is independently selected from H, F, $CH_3$, $CF_3$, $CHF_2$, and $CH_2F$; and m=0–2.

In those formulae I and II, when m=0, it will be appreciated that there is a chemical bond between the silicon and the aromatic ring. It is preferred that m=0 or 1, and more preferably m=1. In those formulae, by "substituted alkyl" or "substituted alkenyl" it is meant that one or more hydrogens of the alkyl or alkenyl group, respectively, is replaced by one or more other substituents. Suitable substituents include, but are not limited to, $(C_1–C_6)$alkyl; substituted $(C_1–C_6)$alkyl; $(C_1–C_6)$alkoxy; alkoxycarbonyls having the general formula $(R^2O—C(O))—$ wherein $R^2$ is as defined herein below; halo; halo$(C_1–C_6)$alkyl such as trifluoromethyl; $(C_1–C_{10})$alkylsulfonate; and arylsulfonate. Fluorine is a preferred halogen substituent. Preferred alkyl and substituted alkyl groups for $R^1$ are $(C_1–C_{10})$alkyl, substituted $(C_1–C_{10})$alkyl, and $(R^2O—C(O))—(C_1–C_{10})$alkyl, wherein $R^2$ is as defined herein below. Preferred substituted $(C_2–C_6)$alkenyl groups for $R^1$ are halo$(C_2–C_6)$alkenyl, and more preferably fluoro$(C_2–C_6)$alkenyl. When $R^1$ is a $(C_1–C_5)$alkyl$(C_6H_4OZ)$ group, as used herein, such Z is referred to as an alkylsulfonato or arylsulfonato substituent, or alternatively as alkylsulfonyloxy of arylsulfonyloxy substituent. The $(C_1–C_6)$alkylsulfonate ester or arylsulfonate ester groups of Z may optionally be substituted, such as by halogen, and particularly fluorine. Suitable groups where $R^1$ is a $(C_1–C_5)$alkyl$(C_6H_4OZ)$ include, but are not limited to, phenylsulfonatobenzyl, phenylsulfonatophenylethyl, methylsulfonatobenzyl, ethylsulfonatobenzyl, propylsulfonatobenzyl, trifluoromethylsulfonatobenzyl, methylsulfonatophenylethyl, tolylsulfonatobenzyl, tolylsulfonatophenylethyl, camphorsulfonatobenzyl, camphorsulfonatophenylethyl, phenylsulfonatophenyl, methylsulfonatophenyl, tolylsulfonatophenyl, camphorsulfonatophenyl, ethylsulfonatophenyl, propylsulfonatophenyl, trifluoromethylsulfonatophenyl, ethylsulfonatophenylethyl, propylsulfonatophenylethyl, trifluoromethylsulfonatophenylethyl, and the like. Other suitable groups for $R^1$ include, but are not limited to, methyl, ethyl, trifluoromethyl, 2,2,2-trifluoroethyl, pentafluoroethyl, phenyl, benzyl, phenethyl, tolyl, trifluoromethylphenyl, methoxyphenyl, trifluoromethoxyphenyl, norbornyl, cyclohexyl, 1,2,2-trifluorovinyl, and the like, and preferably methyl, ethyl, trifluoromethyl, 2,2,2-trifluoroethyl, pentafluoroethyl, phenyl, benzyl, phenethyl, tolyl, trifluoromethylphenyl, trifluoromethoxyphenyl, norbornyl, cyclohexyl, and 1,2,2-trifluorovinyl. Particularly suitable monomers of formula II include, but are not limited to, hydroxyphenyl, hydroxybenzyl and hydroxyphenylethyl. Suitable hydroxy-halo$(C_1–C_6)$alkyl groups for $R^7$ include, but are not limited to, $—C(CF_3)_2OH$.

Photoimageable compositions may be negative-acting or positive-acting. As discussed above, for positive-acting composition, the polymers typically further include one or more monomers containing an acid sensitive or cleavable group. Such acid sensitive monomers that may be polymerized to provide such groups include, but are not limited to, those of the formula III (III)

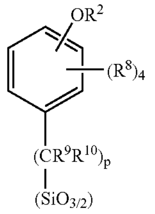

wherein $R^2$ is an acid cleavable group; each $R^8$ is independently selected from H, F, $(C_1–C_6)$alkyl, $(C_1–C_6)$alkoxy, halo$(C_1–C_6)$alkyl, hydroxy-halo$(C_1–C_6)$alkyl or halo$(C_{1-C6})$alkoxy; each $R^9$ is independently selected from H or F; each $R^{10}$ is independently selected from H, F, $CH_3$, $CF_3$, $CHF_2$, and $CH_2F$; and p=0–2. Preferably, p=0 or 1, and more preferably p=1. It is preferred that $R^3$ is ethyl, propyl or cyclohexyl. $R^2$ may be any suitable acid cleavable group. Suitable acid cleavable groups or leaving groups are typically those that readily or facilely form carbonium ions and include, but are not limited to: a) a group selected from $—C(O)OC(CH_3)_3$; $—CH(CH_3)O(C_1–C_6)$alkyl; $—CH_2C(O)OC(CH_3)_3$; $—C_5H_8O$ ("tetrahydropyranyl") or lactones; b) an optionally substituted noncyclic alkyl moiety having 6 or more carbon atoms, with at least 2 carbon atoms selected from secondary, tertiary and quaternary carbon atoms, and wherein the ether oxygen is directly bonded to a quaternary carbon atom; c) optionally substituted fenchyl; d) optionally substituted phenyl; e) optionally substituted 3,2,0 bridged system; f) optionally substituted bridged heteroalicyclic group; g) optionally substituted cycloalkyl group having 3 or 4 ring carbon atoms; and h) optionally substituted 2,2,1-bridged systems. Suitable lactones include those attached to the oxygen by a tertiary carbon, such as γ-valerolactone.

Suitable noncyclic alkyl moieties as leaving groups include those that have one, two or more tertiary carbon atoms, and/or one, two or more quaternary carbons. References herein to a "secondary" carbon indicate the carbon atom has two non-hydrogen substituents (i.e. $CH_2RR'$ where R and R' are the same or different and each is other than hydrogen); references herein to a "tertiary" carbon indicate the carbon atom has three non-hydrogen substituents (i.e. CHRR'R" where R, R' and R" are the same or different and each is other than hydrogen); and references herein to a "quaternary" carbon indicate the carbon atom has four non-hydrogen substituents (i.e. CRR'R"R'" where R, R', R" and R'" are each the same or different and each is other than hydrogen). See, for instance, Morrison and Boyd, Organic Chemistry, particularly at page 85 (3rd ed., Allyn and Bacon), for a discussion of those terms secondary, tertiary and quaternary. It is often preferred that a quaternary carbon is directly linked (i.e. covalently linked with no other interpose atoms) to the oxygen.

Preferred acid cleavable groups of the invention contain only saturated carbon atoms. Thus, e.g., in this preferred aspect of the invention, the groups R, R', R", R'" of the above formulae for secondary, tertiary and quaternary carbons of the groups (i.e. the formulae $CH_2RR'$, CHRR'R", CRR'R"R'") are each saturated alkyl, typically $(C_1–C_{10})$alkyl, more typically $(C_1–C_6)$alkyl, still more typically alkyl having 1, 2, 3 or 4 carbons. Preferred alkyl moieties include those having 1 quaternary carbon linked to the oxygen atom of the ether linkage and one or more additional tertiary or quaternary carbon atoms and not more than a one single ring alicyclic group. Additional preferred alkyl moieties include those having 1 quaternary carbon linked to the ether oxygen atom of the linkage and one or more additional secondary carbon atoms and no more than one ring alicyclic groups.

Optimally, the ether group will contain only carbon and hydrogen atoms and be free of double or triple bonds. More preferred alkyl moieties include those having one quaternary carbon linked to the ether oxygen atom of the linkage and one or more additional quaternary or tertiary carbon atoms and not more than a one single ring alicyclic group. Optimally, the group will contain solely carbon and hydrogen atoms and be free of double or triple bonds. Particularly suitable leaving groups containing a quaternary carbon bonded directly to the oxygen include, but are not limited to, those having the structures of Formulae (IV)–(X), where Ⓟ refers to a polymer.

(IV)

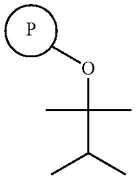

(V)

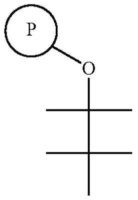

(VI)

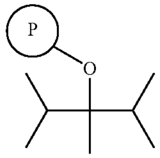

(VII)

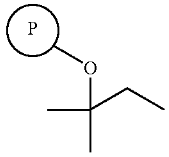

(VIII)

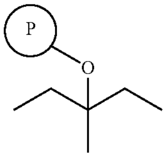

(IX)

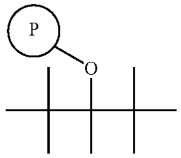

(X)

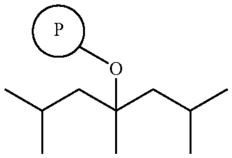

Particularly suitable leaving groups having a quaternary carbon bonded directly to the ether linkage include, but are not limited to, 2,3-dimethyl-2-butyl; 2,3,3-trimethyl-2-butyl; 2-methyl-2-butyl; 3-methyl-3-pentyl; 2,3,4-trimethyl-3-pentyl; 2,2,3,4,4-pentamethyl-3-pentyl; 1-methyl-1-cyclopentyl; 1,2-dimethyl-1-cyclopentyl; 1,2,5-trimethyl-1-cyclopentyl; 1,2,2-trimethyl-cyclopentyl; 2,2,5,5-tetramethyl-1-cyclopentyl; 1-methyl-1-cyclohexyl; 1,2-dimethyl-1-cyclohexyl; 1,2,6-trimethyl-1-cyclohexyl; 1,2,2,6-tetramethyl-1-cyclohexyl; 1,2,2,6,6-pentamethyl-1-cyclohexyl; and 2,4,6-trimethyl4-heptyl.

Additional preferred polymers produced by the methods of the invention include those that contain as polymerized units one or more monomers of formula I, one or more monomers of formula II and one or more monomers of formula III $$(R^1SiO_{3/2}) \quad (I)$$

(II)

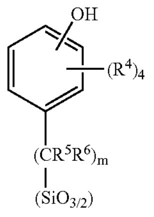

(III)

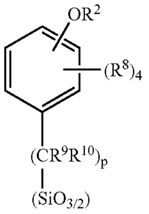

wherein $R^1$ is selected from $(C_1–C_{10})$alkyl, substituted $(C_1–C_{10})$alkyl, $(C_2–C_6)$alkenyl, substituted $(C_2–C_6)$alkenyl, phenyl, $C_6(R^7)_5$, $(C_1–C_5)$alkyl$(C_6(R^7)_4)$, $(C_1–C_5)$alkyl $(C_6H_4OZ)$, vinyl and substituted vinyl; Z is selected from $(C_1–C6)$alkylsulfonate ester or arylsulfonate ester; $R^2$ is an acid cleavable group; each $R^7$ and $R^8$ is independently selected from H, F, $(C_1–C_6)$alkyl, $(C_1–C_6)$alkoxy, halo $(C_1–C_6)$alkyl, hydroxy-halo$(C_1–C_6)$alkyl and halo$(C_1–C_6)$ alkoxy; each $R^4$ is independently selected from $R^7$ and OH; each $R^5$ and $R^9$ is independently selected from H or F; each $R^6$ and $R^{10}$ is independently selected from H, F, $CH_3$, $CF_3$, $CHF_2$, and $CH_2F$; m=0–2; and p=0–2. Particularly suitable polymers for use in positive acting photoimageable compositions are those wherein m=0 or 1. More suitable are those polymers wherein p=0 or 1, and preferably p=1.

In those polymer, the $R^1$ group suitably lowers or helps control the dissolution rate. Thus, increasing the content of the monomers of formula I provides polymers of the present invention having decreased dissolution rate, as compared to the same polymer having a lesser amount of formula I monomers.

In general, the monomers of formulae I–III may be polymerized in any ratio to provide the polymers of the present invention. For example, monomers of formulae I and II may be used in any ratio of I:II from 99:1 to 1:99. Monomers of formulae I and III may be used in any ratio from of I:III from 99:1 to 1:99. When the present polymers are used in positive-acting photoimageable compositions, it is preferred that the monomers of formula III are present from 5 to 80%, based on the total molar percent of the monomers used.

The silicon-containing polymers of the present invention typically have a molecular weight of 500 to 200,000 Daltons, and preferably from 1000 to 100,000 Daltons.

It will be appreciated by those skilled in the art that more than one silicon-containing polymer may be used in the present photoimageable compositions. Thus, the present photoimageable compositions may include one, two or more silicon-containing polymers. When two or more silicon-containing polymers are used, at least one is a silicon-containing polymer of the present invention. The remaining silicon-containing polymers may be conventional silicon-containing polymers or polymers of the present invention. In this way, blends of polymers may be advantageously used in the present photoimageable compositions. Such blends include blends of the present silicon-containing polymers with non-silicon-containing polymers. In these blends, any ratio of polymers is suitable. The specific ratio will depend upon the particular polymers combined and the characteristics (dissolution rate, etch resistance, photospeed, etc.) desired and are within the ability of one skilled in the art.

A wide variety of photoactive components may be used in photoimageable composition of the invention, including, but not limited to, photoacid generators and photobase generators. Photoacid generators are preferred. It will be appreciated by those skilled in that art that more than one photoactive component may be used advantageously in the photoimageable compositions of the present invention.

Photobase generators useful in the present invention are any compounds which liberate base upon exposure to light, typically at a wavelength of about 320 to 420 nanometers, however other wavelengths may be suitable. Suitable photobase generators include, but are not limited to: benzyl carbamates, benzoin carbamates, O-carbamoylhydroxyamines, O-carbamoyloximes, aromatic sulfonamides, alpha-lactams, N-(2-allylethenyl)amides, arylazide compounds, N-arylformamides, and 4-(ortho-nitrophenyl)dihydropyridines.

The photoacid generators useful in the present invention are any compounds which liberate acid upon exposure to light, typically at a wavelength of about 320 to 420 nanometers, however other wavelengths may be suitable. Suitable photoacid generators include halogenated triazines, onium salts, sulfonated esters and halogenated sulfonyloxy dicarboximides.

Particularly useful halogenated triazines include halomethyl-s-triazines. Suitable halogenated triazines include for example, 2-(1-(3,4-benzodioxolyl))-4,6-bis(trichloromethyl)-1,2,5-triazine, 2-(1-(2,3-benzodioxolyl))-4,6-bis (trichloromethyl)-1,3,5-triazine, 2-(1-(3,4-benzodioxolyl))-4,6-bis(tribromomethyl)-1,3,5-triazine, 2-(1-(2,3-benzodioxolyl))-4,6-bis(tribromomethyl)-1,3,5-triazine, 2-(2-furfylethylidene)-4,6-bis(trichloromethyl)-1,3,5-triazine, 2-(2-(5-methylfuryl)ethylidene)-4,6-bis(trichloromethyl)-1,3,5-triazine, 2-(2-(4-methylfuryl)ethylidene)-4,6-bis(trichloromethyl)-1,3,5-triazine, 2-(2-(3-methylfuryl) ethylidene)-4,6-bis-(trichloromethyl)-1,3,5-triazine, 2-(2-(4,5-dimethylfuryl)ethylidene)-4,6-bis(trichloromethyl)-1,3,5-triazine, 2-(2-(5-methoxyfuryl)ethylidene)-4,6-bis (trichloromethyl)-1,3,5-triazine, 2-(2-(4-methoxyfuryl) ethylidene)-4,6-bis(trichloromethyl)-1,3,5-triazine, 2-(2-(3-methoxyfuryl)ethylidene)-4,6-bis(trichloromethyl)-1,3,5-triazine, 2-(2-(4,5-dimethoxy-furyl)ethylidene)-4,6-bis (trichloromethyl)-1,3,5-triazine, 2-(2-furfylethylidene)-4,6-bis(tribromomethyl)-1,3,5-triazine, 2-(2-(5-methylfuryl) ethylidene)-4,6-bis(tribromomethyl)-1,3,5-triazine, 2-(2-(4-methylfuryl)-ethylidene)-4,6-bis(tribromomethyl)-1,3,5-triazine, 2-(2-(3-methylfuryl)ethylidene)-4,6-bis (tribromomethyl)-1,3,5-triazine, 2-(2-(4,5-dimethoxyfuryl) ethylidene)-4,6-bis(tribromomethyl)-1,3,5-triazine, 2-(2-(5-methoxyfuryl)ethylidene)-4,6-bis(tribromomethyl)-1,3,5-triazine, 2-(2-(4-methoxyfuryl)ethylidene)-4,6-bis (tribromomethyl)-1,3,5-triazine, 2-(2-(3-methoxyfuryl)ethylidene)-4,6-bis(tribromomethyl)-1,3,5-triazine, 2-(2-(4,5-dimethoxyfuryl)ethylidene)-4,6-bis(tribromomethyl)-1,3,5-triazine, 2,4,6-tris-(trichloromethyl)-1,3,5-triazine, 2,4,6-tris-(tribromomethyl)-1,3,5-triazine, 2-phenyl-4,6-bis (trichloromethyl)-1,3,5-triazine, 2-phenyl-4,6-bis (tribromomethyl)-1,3,5-triazine, 2-(4-methoxyphenyl)-4,6-bis(trichloromethyl)-1,3,5-triazine, 2-(4-methoxyphenyl)-4,6-bis(tribromomethyl)-1,3,5-triazine, 2-(1-naphthyl)-4,6-bis (trichloromethyl)-1,3,5-triazine, 2-(1-naphthyl)-4,6-bis (tribromomethyl)-1,3,5-triazine, 2-(4-methoxy-1-naphthyl)-4,6-bis(trichloromethyl)-1,3,5-triazine, 2-(4-methoxy-1-naphthyl)-4,6-bis(tribromomethyl)-1,3,5-triazine, 2-(4-chlorophenyl)-4,6-bis(tribromomethyl)-1,3,5-triazine, 2-styryl-4,6-bis(trichloromethyl)-1,3,5-triazine, 2-styryl-4,6-bis(tribromomethyl)-1,3,5-triazine, 2-(4-methoxystyryl)-4,6-bis(trichloromethyl)-1,3,5-triazine, 2-(4-methoxystyryl)-4,6-bis(tribromomethyl)-1,3,5-triazine, 2-(3,4,5-trimethoxystyryl)-4,6-bis(trichloromethyl)-1,3,5-triazine, 2-(3,4,5-trimethoxystyryl)-4,6-bis(tribromomethyl)-1,3,5-triazine, 2-(3-chloro-1-phenyl)-4,6-bis(trichloromethyl)-1,3,5-triazine, 2-(3-chlorophenyl)-4,6-bis(tribromomethyl)-1,3,5-triazine and the like. Other triazine type photoacid generators useful in the present invention are disclosed in U.S. Pat. No. 5,366,846, herein incorporated by reference.

The s-triazine compounds are condensation reaction products of certain methyl-halomethyl-s-triazines and certain aldehydes or aldehyde derivatives. Such s-triazine compounds may be prepared according to the procedures disclosed in U.S. Pat. No. 3,954,475 and Wakabayashi et al., *Bulletin of the Chemical Society of Japan,* 42, 2924–30 (1969).

Onium salts with weakly nucleophilic anions are particularly suitable for use as photoacid generators in the present invention. Examples of such anions are the halogen complex anions of divalent to heptavalent metals or non-metals, for example, antimony, tin, iron, bismuth, aluminum, gallium, indium, titanium, zirconium, scandium, chromium, hafnium, copper, boron, phosphorus and arsenic. Examples of suitable onium salts include, but are not limited to: diaryl-diazonium salts and onium salts of group VA and B, IIA and B and I of the Periodic Table, for example, halonium salts, quaternary ammonium, phosphonium and arsonium salts, aromatic sulfonium salts and sulfoxonium salts or selenium salts. Examples of suitable onium are disclosed in U.S. Pat. Nos. 4,442,197; 4,603,101; and 4,624,912, all incorporated herein by reference. Sulfonium salts such as triphenylsulfonium hexafluorophosphate are preferred.

The sulfonated esters useful as photoacid generators in the present invention include sulfonyloxy ketones. Suitable sulfonated esters include, but are not limited to: benzoin tosylate, t-butylphenyl alpha-(p-toluenesulfonyloxy)-acetate, and t-butyl alpha-(p-toluenesulfonyloxy)-acetate. Such sulfonated esters are disclosed in the *Journal of Photopolymer Science and Technology,* vol. 4, No. 3,337–340 (1991), incorporated herein by reference.

Suitable halogenated sulfonyloxy dicarboximides useful as photoacid generators in the present invention include, but are not limited to:

1(((trifluoromethyl)sulfonyl)oxy)-1H-pyrrole-2,5-dione; N-((perfluorooctanesulfonyl)oxy)-5-norbornene-2,3-dicarboximide; N-((trifluoromethylsulfonyl)oxy)-5-norbornene-2,3-dicarboximide; 1-(((trifluoromethyl)sulfonyl)oxy)-2,5-pyrrolidinedione; 3a,4,7,7a-tetrahydro-2-(((trifluoromethyl)sulfonyl)oxy)-4,7-methano-1H-isoindole-1,3(2H)-dione; 2-(((trifluoromethyl)sulfonyl)oxy)-1H-benz(f)isoindole-1,3(2H)-dione; 3,4-dimethyl-1-(((trifluoromethyl)sulfonyl)oxy)-1H-pyrrole-2,5-dione; 2-(((trifluoromethyl)sulfonyl)oxy)-1H-isoindole-1,3(2H)-dione; 2-(((trifluoromethyl)sulfonyl)oxy)-1H-benz(de)isoquinoline-1,3(2H)-dione; 4,5,6,7-tetrahydro-2-(((trifluoromethyl)sulfonyl)oxy)-1H-isoindole-1,3(2H)-dione; 3a,4,7,7a-tetrahydro-2-(((trifluoromethyl)sulfonyl)oxy)-4,7-epoxy-1H-isoindole-1,3(2H)-dione; 2,6-bis-(((trifluoromethyl)sulfonyl)oxy)-benzo(1,2-c:4,5-c')dipyrrole-1,3,5,7(2H,6H)-tetrone; hexahydro-2,6-bis-(((trifluoromethyl)sulfonyl)oxy)-4,9-methano-1H-pyrrolo(4,4-g)isoquinoline-1,3,5,7(2H,3aH,6H)-tetrone; 1,8,8trimethyl-3-(((trifluoromethyl)sulfonyl)oxy)-3-azabicyclo(3.2.1)octane-2,4-dione; 4,7-dihydro-2-(((trifluoromethyl)sulfonyl)oxy)-4,7-epoxy-1H-isoindole-1,3(2H)-dione; 3-(1-naphthalenyl)-4-phenyl-1-(((trifluoromethyl)sulfonyl)oxy)-1H-pyrrole-2,5-dione; 3,4-diphenyl-1-(((trifluoromethyl)sulfonyl)oxy)-1H-pyrrole-2,5-dione; 5,5'-(2,2,2-trifluoro-1-(triflluoromethyl)ethylidene)bis(2-(((trifluoromethyl)sulfonyl)oxy)-1H-isoindole-1,3(2H)-dione; tetrahydro-4-(((trifluoromethyl)sulfonyl)oxy)-2,6-methano-2H-oxireno(f)isoindole-3,5(1aH,4H)-dione; 5,5'-oxybis-2-(((trifluoromethyl)sulfonyl)oxy)-1H-isoindole-1 ,3(2H)-dione; 4-methyl-2-(((trifluoromethyl)sulfonyl)oxy)-1H-isoindole-1,3(2H)-dione; 3,3,4,4-tetramethyl-1-(((trifluoromethyl)sulfonyl)oxy)-2,5-pyrrolidinedione and mixtures thereof. It is preferred that the halogenated sulfonyloxy dicarboximides comprise one or more of 1 (((trifluoromethyl)sulfonyl)oxy)-1H-pyrrole-2,5-dione; N-((perfluorooctanesulfonyl)oxy)-5-norbornene-2,3-dicarboximide; N-((trifluoromethylsulfonyl)oxy)-5-norbornene-2,3-dicarboximide and 1-(((trifluoromethyl)sulfonyl)oxy)-2,5-pyrrolidinedione, and more preferably N-((perfluorooctanesulfonyl)oxy)-5-norbornene-2,3-dicarboximide or N-((trifluoromethylsulfonyl)oxy)-5-norbornene-2,3-dicarboximide.

In positive-acting systems of the present invention, the photoactive components are typically added to photoimageable compositions in an amount sufficient to generate a latent image in a coating layer of resist material upon exposure to activating radiation. When the photoactive component is a photoacid generator, the amount is typically in the range of 0.1 to 10 percent by weight, based on the weight of the resin, and preferably 1 to 8 percent by weight.

In negative-acting systems of the present invention, the amount of photoactive component useful is any amount sufficient to catalyze cross-linking of the silicon-containing polymer or oligomer. The photoactive components are typically used in the range of 0.1 to 25% by weight, based on the weight of the composition. It is preferred that the photoactive component is present in an amount in the range of 0.1 to 15% by weight, more preferably in the range of 0.1 to 12% by weight, and still more preferably less than equal to 5% by weight. A particularly suitable range is from 0.1 to 5% by weight.

The compositions of the present invention may optionally contain one or more organic cross-linking agents. Negative-acting systems of the present invention preferably include one or more cross-linking agents. Any aromatic or aliphatic cross-linking agent that reacts with the silicon-containing polymer or oligomer is suitable for use in the present invention. Such organic cross-linking agents will cure to form a polymerized network with the silicon-containing polymer or oligomer, and reduce solubility in selected solvents. Such organic cross-linking agents may be monomers or polymers. It will be appreciated by those skilled in the art that combinations of cross-linking agents may be used successfully in the present invention.

Suitable organic cross-linking agents useful in the present invention include, but are not limited to: amine containing compounds, epoxy containing materials, compounds containing at least two vinyl ether groups, allyl substituted aromatic compounds, and combinations thereof. Preferred cross-linking agents include amine containing compounds and epoxy containing materials.

The amine containing compounds useful as cross-linking agents in the present invention include, but are not limited to: a melamine monomers, melamine polymers, alkylolmethyl melamines, benzoguanamine resins, benzoguanamine-formaldehyde resins, urea-formaldehyde resins, glycoluril-formaldehyde resins, and combinations thereof. These resins may be prepared by the reaction of acrylamide or methacrylamide copolymers with formaldehyde in an alcohol-containing solution, or alternatively by the copolymerization of N-alkoxymethylacrylamide or methacrylamide with other suitable monomers. Particularly suitable amine-based crosslinkers include the melamines manufactured by Cytec of West Paterson, N.J., such as CYMEL™ 300, 301, 303, 350, 370, 380, 1116 and 1130; benzoguanamine resins such as CYMEL™ 1123 and 1125; the glycoluril resins CYMEL™ 1170, 1171 and 1172; and the urea-based resins BEETLE™ 60, 65 and 80, also available from Cytec, West Paterson, N.J. A large number of similar amine-based compounds are commercially available from various suppliers. Melamines are the preferred amine-based cross-linkers. Particularly preferred are alkylolmethyl melamine resins. These resins are typically ethers such as trialkylolmethyl melamine and hexaalkylolmethyl melamine. The alkyl group may have from 1 to 8 or more carbon atoms but is preferably methyl. Depending upon the reaction conditions and the concentration of formaldehyde, the methyl ethers may react with each other to form more complex units.

Particularly suitable amine-based cross-linking agents include those of formula IV (IV)

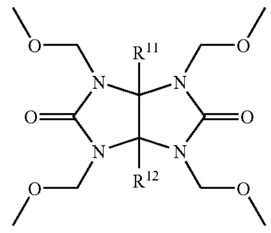

wherein $R^{11}$ and $R^{12}$ are independently selected from H, $(C_1-C_6)$alkyl and phenyl. Preferred alkyl groups for $R^{11}$ and $R^{12}$ are methyl and propyl.

Epoxy containing materials useful as cross-linkers in the present invention are any organic compounds having one or more oxirane rings that are polymerizable by ring opening. Such materials, broadly called epoxides, include, but are not limited to: monomeric epoxy compounds, and polymeric epoxides that may be aliphatic, cycloaliphatic, aromatic or heterocyclic. Preferred epoxy cross-linking materials generally, on average, have at least 2 polymerizable epoxy groups per molecule. The polymeric epoxides include linear polymers having terminal epoxy groups (e.g., diglycidyl ether of a polyoxyalkylene glycol), polymers having skeletal oxirane units (e.g., polybutadiene polyepoxide), and polymers having pendant epoxy groups (e.g., glycidyl methacrylate polymer of copolymer). The epoxides may be pure compounds but are generally mixtures containing one, two or more epoxy groups per molecule.

Useful epoxy-containing materials may vary from low molecular weight monomeric materials and oligomers to relatively high molecular weight polymers and may vary greatly in the nature of their backbone and substituent groups. For example, the backbone may be of any type and substituent groups may be any group free of any substituents reactive with an oxirane ring at room temperature. Suitable substituents include, but are not limited to: halogens, ester groups, ethers, sulfonate groups, siloxane groups, nitro groups, phosphate groups, and the like.

Particularly useful epoxy containing materials in the present invention include glycidyl ethers. Examples are the glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)propane). Such glycidyl ethers include bisphenol A epoxides, such as bisphenol A ethoxylated diepoxide. Further examples of epoxides of this type are described in U.S. Pat. No. 3,018,262, herein incorporated herein by reference to the extent this patent teaches the preparation of such epoxides.

Suitable epoxides useful in the present invention include, but are not limited to: epichlorohydrin, glycidol, glycidylmethacrylate, the glycidyl ether of p-tertiarybutylphenol (e.g., those available under the trade name EPI-REZ 5014 from Celanese); diglycidyl ether of Bisphenol A (e.g., those available under the trade designations EPON 828, EPON 1004 and EPON 1010 from Shell Chemical Co.; and DER-331, DER-332 and DER-334 from Dow Chemical Co.), vinylcyclohexene dioxide (e.g., ERL-4206 from Union Carbide Corp.), 3,4-epoxy-6-methyl-cyclohexylmethyl-3,4-epoxy-6-methylcyclohexene carboxylate (e.g., ERL-4201 from Union Carbide Corp.), bis(3,4-epoxy-6-methylcyclohexylmethyl) adipate (e.g., ERL-4289 from Union Carbide Corp.), bis(2,3-epoxycyclopentyl) ether (e.g., ERL-0400 from Union Carbide Corp.), aliphatic epoxy modified with polypropylene glycol (e.g., ERL-4050 and ERL-4269 from Union Carbide Corp.), dipentene dioxide (e.g., ERL-4269 from Union Carbide Corp.), flame retardant epoxy resins (e.g., DER-580, a brominated bisphenol type epoxy resin available from Dow Chemical Co.), 1,4-butanediol diglycidyl ether of phenolformaldehyde novolak (e.g., DEN-431 and DEN-438 from Dow Chemical Co.), and resorcinol diglycidyl ether (e.g., KOPOXITE from Koppers Company, Inc.).

Compounds containing at least two vinyl ether groups include, but are not limited to divinyl ethers of aliphatic, cycloaliphatic, aromatic or araliphatic diols. Examples of such materials include divinyl ethers of aliphatic diols having from 1 to 12 carbon atoms, polyethylene glycols, propylene glycols, polybutylene glycols, dimethylcyclohexanes, and the like. Particularly useful compounds having at least two vinyl ether groups include divinyl ethers of ethylene glycol, trimethylene-1,3-diol, diethylene glycol, triethylene glycol, dipropylene glycol, tripropylene glycol, resorcinol, Bisphenol A, and the like.

Suitable allyl substituted aromatic compounds useful as cross-linkers in the present invention are those containing one or more allyl substituents, that is, the aromatic compound is substituted at one or more ring positions by the allylic carbon of an alkylene group). Suitable allyl aromatics include allyl phenyl compounds, such as an allyl phenol. An allyl phenol crosslinker can be a monomer or polymer that contains one or more phenol units where the phenol units are substituted at one or more ring positions by an allylic carbon of an alkylene group. Typically the alkylene substituent(s) is propenyl, i.e., the phenol has one or more propenyl substituents. Preferred allyl phenols include a polycondensate of phenol and hydroxybenzaldehyde and an allylhalide such as allylchloride. A number of suitable allyl phenols are commercially available, for example the allyl phenol sold under the trade name THERMAX SH-150AR by Kennedy and Klim, Inc. (Little Silver, N.J.). Allyl phenyl compounds including allyl phenols are also described in U.S. Pat. No. 4,987,264, herein incorporated by reference to the extent this patent teaches the preparation of such compounds.

Particularly suitable organic cross-linking agents include those containing one or more methoxymethyl groups, such as methoxymethyl-substituted melamines and methoxymethyl-substituted glycourils such as those of formula IV, above. Hexamethoxymethylmelamine is a preferred methoxymethyl-substituted melamine. It is further preferred that one or more of the hydrogens of the organic cross-linking agent, and more preferably one or more of the methyl hydrogens in the methoxymethyl substituent, is substituted with a halogen, preferably fluorine. Thus, preferred cross-linkers include those containing one or more methoxyfluoromethyl and/or methoxydifluoromethyl substituents. Exemplary preferred fluorinated cross-linking agents include methoxyfluoromethyl- and methoxydifluoromethyl-substituted melamines and glycourils, such as hexamethoxyfluoromethylmelamine and hexamethoxydifluoromethylmelamine. Also suitable are fluorinated epoxy cross-linking agents. For certain applications, it is preferred that the cross-linking agent is fluorinated.

The compositions of the present invention may suitably comprise only a single type of organic cross-linker, e.g., only an amine containing cross-linker, or may contain two or more different cross-linkers. When a combination of organic cross-linkers is used in the present invention, it is preferred that the combination include an amine containing compound and an epoxy containing compound. The concentration of organic cross-linking agents in the compositions of the present invention may vary within a relatively wide range. It will be appreciated by those skilled in the art that suitable organic cross-linker concentrations will vary with factors such as cross-linker reactivity and specific application of the composition. Typically, the cross-linking agent(s) is present in an amount in the range of 0.1 to 80% by weight, based on the total weight of the composition, preferably in the range of 0.5 to 50%, and more preferably in the range of 1 to 25%. It is preferred that a cross-linking agent is used in the compositions of the present invention.

The photoimageable compositions of the present invention may optionally further include one or more additional components, including, but not limited to, solvents, anti-striation agents, plasticizers, surfactants, base additives, speed enhancers, fillers, dyes and the like. In positive-acting systems, a base additive is typically used to adjust the photospeed of the composition. Such optional additives will be present in relatively minor concentrations in a photoresist composition except for fillers and dyes which may be used in relatively large concentrations, e.g. in amounts of from about 5 to 30 percent by weight, based on the total weight of the composition's dry components.

The photoimageable compositions of the present invention may be readily prepared by those skilled in the art. For example, a photoresist composition of the invention can be prepared by dissolving the components of the photoresist, i.e. polymer binder and photoactive component, in a suitable solvent. Such suitable solvents include, but are not limited to: ethyl lactate, ethylene glycol monomethyl ether, ethylene glycol monomethyl ether acetate, propylene glycol monomethyl ether, propylene glycol monomethyl ether acetate, 3-ethoxyethyl propionate, 2-heptanone, γ-butyrolactone, and mixtures thereof.

Typically, the solids content of the photoresist composition varies from about 5 to about 35 percent by weight, based on the total weight of the composition. The resin binder and photoactive components should be present in amounts sufficient to provide a film coating layer and formation of good quality latent and relief images.

Such photoresist compositions may be applied to a substrate by any known means, such as spinning, dipping, roller coating and the like. When the compositions are applied by spin coating, the solids content of the coating solution can be adjusted to provide a desired film thickness based upon the specific spinning equipment utilized, the viscosity of the solution, the speed of the spinner and the amount of time allowed for spinning.

As discussed above, the present photoimageable compositions are particularly suitable for use as a top layer in a bilayer photoresist system. In such a system, a bottom layer of a conventional photoresist, such as novolac polymer based resist, inert polyarylether-sulfone copolymer based resist or a novolac or polyhydroxystyrene-based thermally cross-linkable system. Such bottom layer is typically applied to or coated on a substrate using any of the above described procedures. The bottom layer is then hard baked such as at 230° C. for 2 minutes, after which the present photoimageable compositions are coated on the cured bottom layer. The bottom layers preferably contain an amount of a UV absorbing component, such as an anthracene dye, sufficient for optical density and etch performance. The bottom layers typically have a thickness of from 0.4 to 1 μm. The top layer of the present photoimageable compositions is typically from 0.05 to 1 μm thick, preferably from 0.1 to 0.5 μm, and more preferably from 0.1 to 0.3 μm.

After being coated on the bottom layer, the present photoimageable composition top layer is dried by heating (baked) to remove any solvent. It is preferably dried until the coating is tack free. Thereafter, it is imaged through a mask in a conventional manner. The exposure is sufficient to effectively activate the photoactive component of the photoresist to produce a patterned image in the resist coating layer, and more specifically, the exposure energy typically ranges from about 1 to 100 $mJ/cm^2$, dependent upon the exposure tool and the components of the photoresist composition.

The photoimageable compositions of the present invention may be activated by a variety of exposure wavelengths, such as 248, 193, 157 nm and 11–15 nm. However, the photoimageable compositions of the present invention may be used with other radiation sources, such as, but not limited to, visible, e-beam, ion-beam and x-ray.

Following exposure, the film top layer of the composition is preferably baked at temperatures ranging from about 70° C. to 160° C. Thereafter, the top layer film is developed to form an etch pattern. The exposed resist film is rendered positive working by employing a polar developer, preferably an aqueous based developer, such as quaternary ammonium hydroxide solutions, such as tetra-alkyl ammonium hydroxide, preferably a 0.15 to 0.26 N tetramethylammonium hydroxide; various amine solutions, such as ethylamine, n-propylamine, diethylamine, triethylamine or methyl diethylamine; alcohol amines, such as diethanolamine, triethanolamine; cyclic amines, such as pyrrole, pyridine, and the like. One skilled in the art will appreciate which development procedures should be used for a given system.

The pattern is next transferred to the underlayer or bottom layer by etching, such as with an oxygen reactive ion etch process. After such processing, the resists, both top and bottom layers, may be removed from the processed substrate using any stripping procedures known in the art The present photoimageable compositions are useful in all applications where photoresists are typically used. For example, the compositions may be applied over silicon wafers or silicon wafers coated with silicon dioxide for the production of microprocessors and other integrated circuit components. Aluminum-aluminum oxide, gallium arsenide, ceramic, quartz, copper, glass, spin-on organic dielectrics, spin-on or chemical vapor deposited inorganic dielectrics, and the like are also suitable employed as substrates for the photoresist compositions of the invention. Other chemical vapor deposited layers, such as cap layers, etch stops and the like, may also be used as substrates.

Alternatively, the present compositions may also be used in optoelectronics applications, such as in the manufacture of optical waveguides. By "optical waveguide" is meant any device that transmits optical radiation across a two-dimensional substrate surface. Suitable optical waveguides include, but are not limited to, splitters, couplers, spectral filters, polarizers, isolators, wavelength division multiplexing structures, and the like. Such waveguides may also contain active functionality, such as amplification and switching such as with electro-optic, thermo-optic or acousto-optic devices. To be useful as amplifiers, the present waveguides typically contain one or more dopants. Erbium is an exemplary dopant. Such dopants are well known in the art. Thus, the present waveguides suitable for use as amplifiers contain one or more dopants.

The waveguides of the present invention may be manufactured as individual waveguides or as an array of waveguides. Whether such waveguides are prepared as an array depends on the particular use and is within the ability of one skilled in the art.

In one embodiment, optical waveguides may be prepared by first disposing a layer of the present compositions on a substrate by any means including, but not limited to, screen coating (or screen printing), curtain coating, roller coating, slot coating, spin coating, flood coating, electrostatic spray, spray coating, dip coating or as a dry film. When the compositions of the present invention are spray coated, a heated spray gun may optionally be used. The viscosity of the composition may be adjusted to meet the requirements for each method of application by viscosity modifiers, thixotropic agents, fillers and the like. Any substrate suitable for supporting a waveguide may be used with the present compositions. Suitable substrates include, but are not limited to, substrates used in the manufacture of electronic devices such as printed wiring boards and integrated circuits. Particularly suitable substrates include laminate surfaces and copper surfaces of copper clad boards, printed wiring board inner layers and outer layers, wafers used in the manufacture of integrated circuits, liquid crystal display ("LCD") glass substrates and the like.

The coated substrate is typically then cured, such as by baking, to remove any solvent. Such curing may be a variety of temperatures, depending upon the particular solvent chosen. Suitable temperatures are any that are sufficient to substantially remove any solvent present. Typically, the curing may be at any temperature from room temperature (i.e., 25° C.) to 170° C. Such curing typically occurs over a period of from 5 seconds to 30 minutes. Such curing may be affected by heating the substrate in an oven or on a hot plate.

After curing, the layer of the present composition disposed on the substrate is then imaged by exposure to actinic radiation through appropriate artwork or a mask. Following exposure, the composition is then cured at a temperature of from 40° to 170° C. Curing time may vary but is generally from about 30 seconds to about 1 hour. While not intending to be bound by theory, it is believed that upon exposure to actinic radiation the silsesquioxane oligomer cross-links, particularly with the optional cross-linking agent. The exposed areas are rendered less soluble than the unexposed areas. Thus, the unexposed areas may be removed, such as by contact with a suitable solvent, aqueous developer or solvent-water mixture, leaving only the exposed areas remaining on the substrate. Suitable aqueous developers include alkali metal hydroxides such as sodium hydroxide and potassium hydroxide in water as well as tetraalkylammonium hydroxide in water. Such developers are typically used in concentrations from 0.1 to 0.3 N, such as 0.15 to 0.26 N tetramethylammonium hydroxide in water. The choice of developer is well within the ability of those skilled in the art. Such development may be at a variety of temperatures such as from room temperature to about 100° C. The time of such development depends upon the material to be removed and the temperature used, but is generally from about 10 seconds to about 1 hour.

Following development, the present waveguides may undergo a final cure step, or re-flow step. In such final cure step, the waveguides may be heated at a temperature in from about 130° to 225° C. in air or inert atmospheres such as nitrogen or argon. Such final cure step aids in removal of residual solvent, removal of hydroxyl groups from the silsesquioxane polymer such as by increasing the extent of cross-linking, alter the waveguide profile such as to reduce surface roughness, and improves the optical transmission properties of the material.

Optical waveguides typically have a core and a cladding, wherein the cladding has a lower index of refraction as compared to the core. Particularly useful waveguides have core having an index of refraction of from 1.4 to 1.55. Typically, suitable cladding has an index of refraction of from 1.3 to 1.54.

It is preferred that a cladding layer is first deposited on a substrate. If the cladding layer is photocurable or thermocurable, it may be blanket cured as a first step. The photodefinable core material is then deposited on the cladding layer, imaged and the unexposed areas optionally removed. A second cladding layer is then deposited on the imaged waveguide. The second cladding layer may be the same or different from the first cladding layer. However, the indices of refraction of the first and second cladding layers should be the same. The second cladding layer is then cured, or imaged in the case of a photocurable cladding composition, to provide a waveguide structure.

The silsesquioxane oligomers and polymers of the present invention are suitable for use in the cladding and/or core of the present optical waveguides. Preferably, the present photodefinable compositions are used to prepare cores for optical waveguides. It will be appreciated that the refractive index of a photodefinable composition including a present silsesquioxane oligomer and one or more organic cross-linking agents may be modified by changing the amount and type of the one or more cross-linking agents selected and/or photoactive component. Thus, the present compositions may be useful as core or cladding material depending upon the type and quantity of cross-linking agents selected.

All documents mentioned herein are incorporated herein by reference. The following non-limiting examples are illustrative of the invention.

EXAMPLE 1

Synthesis of Silane Monomer of α-methyl, 4-acetoxybenzyl trichlorosilane

A 50 ml 2 necked round bottomed flask equipped with refluxing condenser and an addition funnel is flushed with nitrogen for 10 minutes and charged with 10 mg of $Pd(OAC)_2$ and 40 mg of triphenylphosphine and 10 ml of toluene. The mixture is stirred at room temperature. 2 g of p-acetoxystyrene is added (all at once) to the clear solution followed by dropwise addition of 4.5 g trichlorosilane. The whole mixture was stirred at 50° C. for 10 hours after which solvent and the unreacted starting materials removed by distillation. The crude product of α-methyl, 4-acetoxybenzyl trichlorosilane is evaluated by $^{1}H$ and $^{13}C$ NMR and produced in 95% yield.

EXAMPLE 2

Polymer Synthesis Using α-methyl, 4-acetoxybenzyl trichlorosilane

A solution of known amounts of 1,4-phenylenediamine, triethylamine and excess THF are added drop wise to a three necked flask containing known amount of α-methyl, 4-acetoxybenzyl trichlorosilane in known amount of toluene at −15° C. This solution is stirred for 30 min at low temperature (−15° C.) after which a known amount of water and triethylamine and THF are added drop wise to the flask at −5° C. This mixture is stirred at this temperature for additional 3 h then washed with water until neutral and dried with anhydrous sodium sulfate overnight.

The final solution from the above reaction is stirred in the presence of molecular sieves (4 angstroms) and a catalytic amount of triethylamine at 50° C. for 72 h. After 72 h, the polymer solution is washed with water until neutral and the solvent was distilled off. The solid polymer was dissolved in minimum amount of THF and precipitated in water (twice) and dried in vacuum at 50° C. for 24 h.

EXAMPLE 3

Photoresist Preparation and Lithographic Processing

A preferred bilayer resist composition was prepared and processed as follows.

Top Layer

The top resist layer was formulated at 10 weight percent solids. The following components were admixed to provide the resist composition: polymer, base additive, surfactant, and photoacid generator component.

Polymer, base additive (Troger's base) and surfactant (RO-8 surfactant) are added as solutions of propylene glycol methyl ether acetate (PGMEA). The photoacid generator is added as a solution in ethyl lactate. The final solvent blend of the formulated resist was 90:10 v/v PGMEA:ethyl lactate. The polymer is as produced in Example 2 above. The photoacid generator component consists of MDT in an amount of 6.5 weight percent of total solids (all resist components except solvent) and t-butylphenyldiphenyl sulfonium trifluorobenzenesulfonate in an amount of 2.9 weight percent based on total solids. The base additive (Troger's base) is present in an amount of 0.563 weight percent based on total solids. The surfactant (R-08; from 3M) is present in an amount of 0.2 weight percent based on total solids.

Bottom Layer

The bottom layer composition is formulated at 18.26 weight percent solids. All components are added as solutions in either PGMEA or ethyl lactate, with a final solvent blend of 80:20 v/v PGMEA:ethyl lactate.

The bottom layer composition consists of components of polymer, crosslinker, thermal acid generator and surfactant. The polymer component consists of a resin blend of a phenolic novolac resin and a copolymer containing anthracene methyl acrylate, hydroxyl ethyl methacrylate and methyl methacrylate. The crosslinker is a benzaquanaminc resin (Cymel 1170) which is present as 15 weight percent of total solids of the bottom layer composition. The thermal acid generator is Nacure 5524 which was present as 4 weight percent of total solids. The surfactant is R-08 which was present as 0.3 weight percent of total solids.

The compositions are lithographically processed as follows. The bottom layer composition is spin coated onto silicon wafers and cured at 175° C. for 60 seconds to provide coating layers of 5100 angstrom thickness. The top layer composition is then spin coated over the bottom layer and soft-baked at 90° C. for 90 seconds. The applied resist layer is then exposed to 248 nm radiation through a photomask, post-exposure baked at 90° C. for 90 second, and developed with 0.26 N aqueous alkaline solution.

The foregoing description of the invention is merely illustrative thereof, and it is understood that variations and modification can be made without departing from the spirit or scope of the invention as set forth in the following claims.

What is claimed is:

1. A method for preparing a chemically-amplified positive photoresist composition, comprising:

a) producing a monomer by reaction of reagents comprising a vinyl carbocylic carboxylic aryl ester and a silane compound and polymerizing the monomer to provide a siloxane polymer; and b) admixing the polymer with a photoactive component to provide a chemically-amplified positive photoresist.

2. The method of claim 1 wherein the carbocyclic aryl compound is a substituted phenyl compound.

3. The method of claim 2 wherein the phenyl group is 1,4-substituted or 1,3-substituted.

4. The method of claim 1 wherein the carbocyclic aryl compound has the formula $CH_2$=CH—$C_6H_4$-ester.

5. The method of claim 4 wherein the ester is —OC(=O)R wherein R is optionally substituted $C_{1-6}$alkyl.

6. The method of claim 4 wherein the ester is —OC(=O)$CH_3$.

7. The method of claim 1 wherein the silane compound is selected from the group consisting of a trihalosilane, a trihydroxysilane, and a trialkoxysilane.

8. The method of claim 1 wherein the silane compound is a trihalosilane.

9. The method of claim 1 wherein the silane compound is a trichlorosilane.

10. The method of claim 1 wherein the silane compound and the carbocyclic aryl compound arc reacted in the presence of a phosphine reagent.

11. The method of claim 1 wherein the silane compound and the carbocyclic aryl compound are reacted in the presence of a metal catalyst.

12. The method of claim 11 wherein the silane compound and the carbocyclic aryl compound are reacted in the presence of a palladium compound.

13. The method of claim 12 wherein the palladium compound is a Pd(II) compound.

14. The method of claim 1 wherein the siloxane polymer is obtained by polymerizing the monomer in the presence of compound having multiple reactive nitrogen moieties to provide the siloxane polymer.

15. The method of claim 1 wherein the carbocylic aryl compound and the silane compound are reacted in the presence of a phosphine reagent and a metal catalyst.

16. A compound that is $CH_3(SiCl_3)CH$—$C_6H_4$-ester.

17. The compound of claim 16 wherein the ester is —OC(=O)R wherein R is optionally substituted $C_{1-6}$alkyl.

18. A method for producing a positive-acting photoresist composition comprising:

(a) providing a Si polymer by steps comprising producing a monomer by reaction of reagents comprising (i) a vinyl carbocyclic phenyl ester compound that is 1,4-substituted or 1,3-substituted and (ii) a reactive silane compound;

(b) polymerizing the monomer to provide the Si polymer; and (c) admixing the polymer with a photoactive component to provide a positive-acting photoresist composition.

* * * * *